United States Patent
Angeletakis

(10) Patent No.: US 9,044,288 B2
(45) Date of Patent: Jun. 2, 2015

(54) POLYVINYLSILOXANE BASED CURABLE DENTAL RETRACTION COMPOSITION

(71) Applicant: DENTSPLY International Inc., York, PA (US)

(72) Inventor: Christos Angeletakis, Orange, CA (US)

(73) Assignee: DENTSPLY International Inc., York, PA (US)

(*) Notice: Subject to any disclaimer, the term of this patent is extended or adjusted under 35 U.S.C. 154(b) by 0 days.

(21) Appl. No.: 14/133,703

(22) Filed: Dec. 19, 2013

(65) Prior Publication Data

US 2014/0170596 A1    Jun. 19, 2014

Related U.S. Application Data

(60) Provisional application No. 61/739,636, filed on Dec. 19, 2012.

(51) Int. Cl.
*A61K 6/10* (2006.01)
*A61C 9/00* (2006.01)
*A61K 6/00* (2006.01)

(52) U.S. Cl.
CPC .............. *A61C 9/0033* (2013.01); *A61K 6/0011* (2013.01); *A61K 6/0014* (2013.01); *A61K 6/0067* (2013.01); *A61K 6/0073* (2013.01)

(58) Field of Classification Search
CPC ..................... A61K 6/0011; A61K 6/0014
USPC ........................................ 523/105, 109, 113
See application file for complete search history.

(56) References Cited

U.S. PATENT DOCUMENTS

| | | |
|---|---|---|
| 6,040,354 A | 3/2000 | Hubner et al. |
| 6,121,362 A | 9/2000 | Wanek et al. |
| 6,652,840 B1 | 11/2003 | Prevendar |
| 7,195,483 B2 | 3/2007 | Dragan |
| 7,549,862 B2 | 6/2009 | Kollefrath et al. |
| 8,470,905 B2 | 6/2013 | Dragan et al. |
| 2009/0061393 A1 | 3/2009 | Kollefrath et al. |
| 2012/0329006 A1 | 12/2012 | Pierson et al. |

OTHER PUBLICATIONS

International Search Report, Application No. 2013/076328, Published Dec. 19, 2013.
International Written Opinion, Application No. 2013/076328, Published Dec. 19, 2013.

*Primary Examiner* — Edward Cain
(74) *Attorney, Agent, or Firm* — Leana Levin; Douglas J. Hurq; David A. Zdurne

(57) ABSTRACT

Disclosed herein is a two part retraction system that can be inserted into the sulcus to form a semi-rigid porous elastomer releasing a hemostatic agent suitable for sulcus retraction such that a dental impression may be completed by a dental practitioner.

14 Claims, No Drawings

POLYVINYLSILOXANE BASED CURABLE DENTAL RETRACTION COMPOSITION

This application claims priority U.S. Provisional Patent Application No. 61/739,636, filed Dec. 19, 2012.

FIELD

A gingival retraction system is presented using a 2 part addition curing silicone composition. This syringable silicone contains a hemostatic agent and expands in volume during curing by releasing hydrogen gas. A semi-rigid foam is produced within a few seconds after extrusion. The cured material is removed easily in one piece without rinsing.

BACKGROUND

In dental treatment a cord can be used for retracting gingiva from a prepared tooth. This cord is named a retraction cord and is packed between gingival tissue and the margin of the prepared tooth (this region is also called sulcus) using an appropriate dental instrument. This procedure however may be cumbersome and can result in discomfort to the patient and also may cause inaccurate margins for the final restoration.

For a more convenient placement retraction pastes are used. The retraction pastes currently commercially available are based on an aqueous clay suspension of a hemostatic agent such as aluminum chloride (Expasyl by Kerr Corporation, Orange Calif. or Retraction Capsule by 3M Espe Minneapolis Minn.). However these pastes must be rinsed after placement adding another step. Moreover, if insufficient rinsing is done, curing of adhesive placed afterward at the site may be negatively affected.

Gingival retraction systems based on a 2-part addition silicone are also available. One such system is Gingitrac Mini-Mix by Centrix, Shelton Conn. This material contains an aluminum based astringent. However, after syringing to the site, a foam cap must be used to press the material into the sulcus. This is an additional step to the procedure.

U.S. Pat. No. 5,676,543 describes a moldable material formed over teeth with a second flowable material containing an astringent placed into the impression of the teeth in the moldable material providing retraction and hemostasis at the gum line. A moldable material, preferably a silicone, may contain an astringent such as aluminum ammonium sulfate is made into a mold of teeth. The impression formed in the mold of the teeth is filled with a less viscous or initially flowable material also containing an astringent. The mold with the flowable material is placed over the teeth. The initially flowable material preferably sets into a solid. The flowable material may be made of a condensation silicone having a base and catalyst. The mold helps to apply pressure to the flowable material which is transmitted to the gum tissue resulting in retraction and hemostasis.

U.S. Pat. No. 7,195,483 describes a method and a device for effecting the cordless retraction of the gingival sulcus tissue prior to the taking of an impression of a tooth for making a crown or bridge which is attained by controlling any bleeding in the gingival sulcus area, and utilizing a dental dam preferably formed of a sponge or foam like material to contain an astringent fortified silicone impression material embedded about the prepared tooth, and using the patient's biting force to apply the necessary pressure onto the dam until the silicone impression material sets and adheres to the dam to enhance easy removal of the set impression material from the tooth. The dam is formed to accommodate either the posterior teeth or the anterior teeth. The dam has retainers formed therein for aiding in holding the silicone impression material.

U.S. Pat. No. 8,470,905 describes a method and a device for effecting the cordless retraction of the gingival sulcus tissue that includes a dam shaped to be fitted onto a tooth. In one embodiment, the well of the dam is pre-filled with a predetermined amount of a flowable retraction material having a heavy viscosity or putty consistency. In another embodiment a hydrophilic material is added. The preloaded tooth dam is fitted to a prepared tooth so that when pressure is applied onto the tooth dam, the retraction material is displaced under pressure and forced into the sulcus, causing the gingival tissue to retract away from the tooth to enlarge the gingival sulcus. In another embodiment the cap is filled with a dilatant material. In another embodiment, the cap is filled with an impregnated compressible porous material. In yet another embodiment, the cap is pre-dosed with an astringent or hemostatic agent.

U.S. Pat. No. 7,549,862 describes a process of retraction of sulcus, comprising the steps of: applying a silicone material onto and/or at the vicinity of the boundary of a tooth and adjacent sulcus, which silicone material expands during or after its curing reaction; applying a cap onto said tooth, thereby forming a chamber over said silicone material, wherein said chamber comprises as its walls the tooth, the cap and an outer section of said sulcus; whereby said chamber allows for the silicone material to expand into the crevice between sulcus and tooth. Said cap is at least partially filled with a plastically deformable material when applied onto said tooth in step; and/or said cap is deformable, especially under biting pressure.

There is still a need to achieve good retraction of the gingiva using paste delivery with a convenient reduced step procedure that does not rely on a compression cap or a rinsing step.

SUMMARY

A gingival retraction system is presented using a two part room temperature addition curable silicone system. Semi-rigid foam is produced within a few seconds after extrusion of this two-part system via a hydrosilation reaction and other crosslinking reactions resulting in the formation of hydrogen gas in addition to a crosslinked network. The volume expansion caused by hydrogen release assists in the retraction of the sulcus by providing additional pressure. To enhance stability of the composition before mixing, a hemostatic agent present in the catalyst paste may be encapsulated using a shell made of a water soluble polymer such as gelatin so it will quickly dissolve when exposed to oral fluids. This water soluble polymer is optional. Hydrophilic additives such as potassium acrylate can be added to enhance the release of the aluminum ion from the hemostatic agent. For delivery a double barrel syringe may be used. Accurate intraoral delivery into the sulcus is accomplished with a mixing tip that ends in a long slim nozzle with an internal diameter of less than 1 mm possibly with an orientation ring similar in size and position to a perio probe. The cured material is removed easily in one piece without rinsing and without the need for a cord.

DETAILED DESCRIPTION

Two part polyvinylsiloxane (addition silicone) compositions containing a crosslinker that is high in active hydrogen content are described herein. These crosslinkers are typically trimethylsiloxy terminated polymethylhydrosiloxanes or trimethylsiloxy terminated polymethylhydrosiloxane-dimethylsiloxane copolymers. The hydride terminated analogues of these copolymer types can also be used. These compositions give a large amount of hydrogen gas during cure resulting in a semi-rigid foam within a few seconds after extrusion from a mixing tip. The expansion is at least 20% after cure. These two part compositions include a base paste and a catalyst paste.

In embodiments, the base paste includes (1) a crosslinker capable of releasing hydrogen gas upon combination with a catalyst paste having a hydrosilation catalyst at room temperature, (2) a vinyl fluid, (3) a non-reinforcing filler, (4) a reinforcing filler, (5) optionally a hydroxy terminated polydimethylsiloxane and (6) optionally a hydrophilic additive.

In embodiments, the catalyst paste includes (1) a vinyl fluid, (2) a hemostatic agent, (3) a non-reinforcing filler, (4) a reinforcing filler, (5) a platinum complex hydrosilation catalyst, and (6) a retarder.

Upon mixing of the two pastes, polymerization, or curing, of these formulations is accompanied by the release of hydrogen gas giving a semi-rigid foam. This foam has sufficient strength to displace or deflect gingival tissue when applied into the sulcus.

In embodiments, the base paste includes a polymethylhydrosiloxane crosslinker which is capable of releasing hydrogen gas upon combination with a catalyst paste having a hydrosilation catalyst at room temperature. Any hydrosiloxane type crosslinker is suitable for use herein so long as the active hydrogen content of the siloxane is at least 7 mmol/g or at least 10 mmol/g. The crosslinker may be present in the base paste in amounts of from about 5 to about 11 weight percent of the base paste, or from about 7 to about 9 weight percent of the base paste.

The base and/or catalyst paste may further include a vinyl fluid for forming the elastomer via a hydrosilation reaction. Vinyl fluids are vinyl terminated organopolysiloxanes having at least about two vinyl groups per molecule. Tertiary or quadrifunctional substitutions of the vinyl groups are possible. Preferred for use herein are linear vinyl terminated organopolysiloxanes. Most commonly-used vinyl terminated organopolysiloxanes have a methyl substituent, for example, vinyl terminated polydimethylsiloxane. Other substituents such as alkyl, aryl, halogen, and the like may also be included. This vinyl fluid is used in amounts of from about 30 weight percent to about 60 weight percent, such as from about 35 weight percent to about 50 weight percent of the total amount of base and/or catalyst paste.

The base and/or catalyst paste may further include a filler material. The filler material may include a non-reinforcing filler material such as crystalline silica such as Cristobalite silica, diatomaceous earth, alumina, magnesia, titanium dioxide, calcium carbonate, metallic oxides, and the like. The filler may further include a reinforcing filler, such as fumed silica, carbon black, and the like. The non-reinforcing filler material may be present in the base paste in amounts of from about 40 weight percent to about 60 weight percent or from about 45 weight percent to about 55 weight percent. The reinforcing filler material may be present in the base paste in amounts of from about 0.25 weight percent to about 5 weight percent or from about 0.25 weight percent to about 5 weight percent of the total amount of base and/or catalyst paste.

The base paste may further include a hydroxy terminated polydimethylsiloxane, such as a silanol fluid, in amounts of from about 0 to about 50 weight percent to impact higher flexibility and lower hardness. When present, the silanol fluid may be present in the base paste in amounts of 2 weight percent to about 50 weight percent or from about 25 weight percent to about 45 weight percent as a substitute of the vinyl fluid.

The base paste may further optionally include a hydrophilic additive to enhance the release of the aluminum ion from the hemostatic agent. Potassium polyacrylate is one example of such a hydrophilic additive that can be included in the formulation. Other hydrophilic additives may also be used, such as sodium polyacrylate, other polyelectrolytes or siloxylated polyethers. When present, the hydrophilic additive may be present in the base paste in amounts of 0.1 weight percent to about 10 weight percent or from about 0.5 weight percent to about 5 weight percent as a substitute of the vinyl fluid.

In embodiments, the catalyst paste includes at least one hemostatic agent. Hemostatic agents (also called astringent agents) that may be useful in assisting hemostasis include, but are not limited to, aluminum compounds such as potassium aluminum sulfate (AlKSO4) present in the anhydrous or the dodecahydrate form, aluminum ammonium sulfate, aluminum sulfate, aluminum chlorohydrate, aluminum acetate, other water soluble astringent aluminum salts, and mixtures thereof. Another class of hemostatic agents that may be used in the catalyst paste described herein are iron-based compositions such as ferric salts, including but not limited to ferric sulfate, ferric chloride, and mixtures thereof. Other hemostatic agents further include permanganates and zinc chloride. Also organic hemostatic agents may be used like tannins, adrenaline or 8-hydroxyquinoline derivatives. The hemostatic agent may be present in the catalyst paste in amounts of from about 3 to about 10 weight percent of the catalyst paste, or such as from about 5 to about 8 weight percent of the catalyst paste. These hemostatic agents are optionally encapsulated and/or may be also present in the base paste.

The catalyst paste may further include a hydrosilation catalyst, such a a platinum catalyst, more specifically such as Karstedt's catalyst (1% Pt), which may be present in amounts of from about 0.01 to about 1 weight percent of the catalyst paste, such as from about 0.1 to about 0.5 weight percent of the catalyst paste.

In embodiments, the catalyst paste may include a retarder or inhibitor. Examples of suitable retarders include tetravinyl-octamethyl-cyclo-tetrasiloxane (vinyl D4) and divinyltetramethyldisiloxane (DVTMDS). In embodiments, the retarder may be present in the catalyst paste in amounts of from about 0.01 weight percent to about 0.5 weight percent or in amounts 0.2 weight percent to about 0.4 weight percent.

The formulation of mixed base and catalyst pastes may be thick enough to deflect or displace the gingival tissue when injected into the sulcus. A suitable viscosity range for the mixed formulation is from about 10000 to about 30000 Pa·s. A particular rheological parameter that describes the ability of the material to displace gingival tissue is the storage modulus as measured using a stress rheometer in the oscillatory mode. The value of storage modulus may be above 2000 kPa.

EXAMPLE

A formulation example is shown in Table 1 below.

|  | Fast Set Parts Total | Regular Set Parts Total |
|---|---|---|
| Base | BE9-76-1 | BE9-76-1 |
| Vinyl Fluid 4000 csk | 40 | 40 |
| Polymethylhydrosiloxane, 14 mm/g | 7 | 7 |
| Cristobalite silica | 52 | 52 |
| Hydrophobic fumed silica | 1 | 1 |
| Total | 60 | 60 |
| Catalyst | BE9-76-2 | BE9-82-1 |
| Vinyl silicone fluid 4000 csk | 44.5 | 43.75 |
| Karstedt's Catalyst (1% Pt) | 0.25 | 0.25 |
| Vinyl D4 Retarder (10% solution in Vinyl fluid 1000 csk) | 2.25 | 3 |
| Aluminum Potassium Sulfate dodecahydrate (AlKSO4) ground | 7 | 7 |
| Cristobalite silica | 45 | 45 |
| Hydrophobic fumed silica | 1 | 1 |
| Total | 100 | 100 |
| Working time (sec) | 45/100 | 75/160 |

The hemostatic agent AlKSO4 was obtained from Aldrich (Milwaukee Wis.) and then ground to a particle size less than 100 microns and dispersed in the catalyst side of a 2-part addition silicone as shown in the above example.

The properties for this formulation and a comparison with commercially available products are shown in Table 2 below.

| Physical Property Comparison | Retraction Material-EXP | Gingitrac (Centrix) | Magic FoamCord (Coltene) | ADA Specification #19-Type 1 |
|---|---|---|---|---|
| Lot # | BE9-76 (BAH45-53) | A18147 |  |  |
| WT/ST sec. | 48/108 | 150/300 | 60/300 |  |
| Mix Consistency, mm | 31.5 | 32 |  | 35 max |
| Shore A Hardness @ 60 minutes | 66 | 49 |  |  |
| Tensile Tear Strength, psi mean (sd) | 332 (12) | 125 (5) |  |  |
| Tensile Stress, Mpa | 3.6 (0.2) | 1.9 (0.1) |  |  |
| Ultimate Elongation, % | 55 (2) | 122 (9) |  |  |
| Recovery (%) @ MRT | MRT 2' 99.75 | MRT 5' 98.85 |  | min 96.5 |
| Strain in Compression (%) | 2.2 | 3.2 |  | 0.8-20 |
| Linear Dimensional Change (%) Immediate | 0.72* | 0.02* |  | 1.5 max |

MRT = Mouth Removal Time

The "Retraction Material—EXP" above is an example of the two-part retraction system described herein. Gingitrac® is a retraction system sold by Centrix, and Magic Foam-Cord® is a retraction system sold by Coltene. The foam concentration in Magic FoamCord® was too high to prepare proper physical strength test specimens such as for tensile strength so were not measured.

Expansion Measurement:

A test was done to compare the expansion of the EXP retraction material and the two commercial retraction materials. Thus in a 10 ml graduated cylinder, 3.9 g of mixed retraction material was placed. Immediately water was added to bring the total volume to 3.0 ml. Two samples were done for each material. After 5 minutes the volume was measured again. The results were: EXP: 3.9, 3.6. Gingitrac 3.0, 3.0 (no expansion), Magic FoamCord 3.5, 3.4. The results indicate that there was substantial expansion for EXP and Magic Foam Cord.

Aluminum Release Measurement:

The water supernatant from the above expansion measurements was tested for aluminum content. A standard colorimetric method was used (Smith W. H., Sage E. E., Siewers I. J., J. Anal. Chem. 1949, 21, 1334). The results for aluminum ion concentration are expressed in micromoles/titer: EXP: 0.89, Gingitrac 34.0, Magic FoamCord 0.051, distilled water 0.0081. The results indicate that although Gingitrac has the highest Aluminum ion release, EXP had an Aluminum ion release over 10 times the one of Magic FoamCord. This is consistent with the product literature since Magic FoamCord does not claim release of Aluminum ion.

The polymerization (curing) of these formulations is accompanied by the release of hydrogen gas giving a semi-rigid foam. This foam has enough strength to displace or deflect gingival tissue when applied into the sulcus.

It may be advantageous to encapsulate the hemostatic agent to enhance the stability of the formulation. A water soluble polymer that is insoluble in silicones is the preferred shell material. A water soluble polymer that is particularly preferred is gelatin. Microcapsules where the hemostatic agent is in the core and gelatin is used as the shell material will work well for two reasons: The gelatin is completely insoluble in the silicone phase assuring stability and the gelatin dissolves quickly in the presence of aqueous fluids such as blood and saliva, allowing the hemostatic agent to cause hemostasis. The microcapsules can be prepared via various methods familiar to those skilled in the art of encapsulation and are sized to be smaller than 100 μm. One such method would be to dissolve the hemostatic agent along with the water soluble polymer and spray dry or precipitate it such that it will form a polymer shell around the inorganic material. This encapsulated powder then can be re-dispersed in a silicone based fluid that is part of the final formulation. Another method is to use a fluidized bed and spray an aqueous solution of the water soluble polymer on the hemostatic agent particles followed by drying.

It also may be advantageous to add hydrophilic additives to enhance the release of the Aluminum ion from the hemostatic agent. Potassium polyacrylate is one example of such a hydrophilic material that can be included in the formulation. Other hydrophilic materials may also be used, such as sodium polyacrylate, other polyelectrolytes or siloxylated polyethers.

The loading (or concentration of the fillers) in the final paste is adjusted to give a final viscosity of the formula is about 10000 to 30000 Pa·s. Typical fillers used in impression materials can be used such as silica, diatomaceous earth, talc and the like.

Delivery System:

The system consists of a two part double barrel syringe at a mixing ratio of 1:1 to 10:1 with a mixing tip that ends in a long slim nozzle tapered at the end to gain access into the sulcus. The internal diameter at the end is less than about 1 mm, such as from about 0.5 mm to about 0.8 mm, to allow delivery into the sulcus and the outer diameter is kept at a minimum. Although a hand delivery device can be used, mechanically assisted devices such as described in Patent Application Publication No. US2012/0329006, which is incorporated herein in its entirety by reference, can be used.

The loading of the fillers is adjusted so the paste has enough viscosity to deflect the gingival tissue or otherwise said to create a "closed space" between the gingiva and the tooth. However, this viscosity must also result in a low enough extrusion force that will allow convenient application. This tip can contain an orientation ring at 3 mm from the tip, similar in size and position to a perio probe making for accurate intraoral delivery. For example, a 2.5 ml Mixpac® syringe (Sulzer Co. Grabs, Switzerland) can be used with a custom plastic tip with the required dimensions at the end to correspond to the perio probe. A Mixpac dispenser can provide the required extrusion force.

Alternatively, another possible such system is the u-TAH Nano by Nordson (East Providence, R.I., http://www.nordson.com/en-us/divisions/efd/products/tah/cartridge-systems/Pages/u-tah-nano.aspx). The dispenser for this system may allow for more extrusion force so a higher viscosity paste can be used that may be advantageous for delivery into the sulcus.

Other delivery systems are possible as long as long as they allow good mixing of a 2 part system and delivery through a tip that is smaller than 2 mm and preferably less than 1.5 mm in internal diameter.

In embodiments, the two part retraction system is placed in a specific package for the storage and dispensing for a plurality of materials, such as that described in U.S. Pat. No. 8,016,161, which is incorporated herein in its entirety by reference. For example, such a package or dispensing cartridge includes first and a second longitudinally juxtaposed barrels; each said barrel having a first and a second end; each said first and second barrels having a quantity of at least one of the materials initially contained therein; each said barrel having an open end and a dispensing end; a sealing plunger disposed in each said barrel such that the material in each said barrel is initially positioned between said dispensing end of said barrels and the respective ones of said sealing plungers; a snap cap contiguously formed to initially close each of said dispensing ends of said barrels; such that said snap cap may be broken from said barrels to form a secondary open end at said dispensing end of said barrels, thereby facilitating the material contained in each said barrel to flow through and be dispensed; wherein the dispensing ends and the snap cap form a neck area as a section of reduced thickness which is defined by a V-groove that runs around the perimeter of the neck area in a figure 8 shape, whereby the V-groove acts to concentrate the stress across the neck in such a way that said snap cap may be broken from said barrels along a breaking plane; wherein said snap cap includes a tab portion opposite the neck area, the tab portion being of a sufficient size to allow a user to apply enough leverage to the tab portion to break said snap cap at the section of reduced thickness.

The dispensing cartridge described above can be utilized with any known, suitable dispensing device. For example, the cordless, pneumatic dispensing device described in co-owned U.S. Patent Application Publication No. 2012/0329006, which is incorporated herein in its entirety by reference, is suitable for use herein.

While only certain features and embodiments of the invention have been shown and described, many modifications and changes may occur to those skilled in the art (for example, variations in sizes, dimensions, structures, shapes and proportions of the various elements, values of parameters (for example, temperatures, pressures, etc.), mounting arrangements, use of materials, colors, orientations, etc.) without materially departing from the novel teachings and advantages of the subject matter recited in the claims. The order or sequence of any process or method steps may be varied or re-sequenced according to alternative embodiments. It is, therefore, to be understood that the appended claims are intended to cover all such modifications and changes as fall within the true spirit of the invention. Furthermore, in an effort to provide a concise description of the exemplary embodiments, all features of an actual implementation may not have been described (i.e., those unrelated to the presently contemplated best mode of carrying out the invention, or those unrelated to enabling the claimed invention). It should be appreciated that in the development of any such actual implementation, as in any engineering or design project, numerous implementation specific decisions may be made. Such a development effort might be complex and time consuming, but would nevertheless be a routine undertaking of design, fabrication, and manufacture for those of ordinary skill having the benefit of this disclosure, without undue experimentation.

I claim:

1. A two part retraction system comprising:
   a base paste and a catalyst paste, wherein
   the base paste comprises (1) a crosslinker capable of releasing hydrogen gas upon combination with the catalyst paste having a hydrosilation catalyst at room temperature, (2) a vinyl fluid, (3) a non-reinforcing filler, (4) a reinforcing filler, (5) optionally a hydroxy terminated polydimethylsiloxane, and (6) optionally a hydrophilic additive, and
   the catalyst paste comprises (1) a vinyl fluid, (2) a hemostatic agent, (3) a non-reinforcing filler, (4) a reinforcing filler, (5) a platinum complex hydrosilation catalyst, and (6) a retarder,
   wherein the hemostatic agents is ferric sulfate, ferric chloride, a mixture of ferric sulfate and ferric chloride, permanganates, zinc chloride or a water soluble astringent aluminum salt.

2. The two part retraction system of claim 1, wherein the crosslinker has a hydrogen content of at least 7 mmol/g.

3. The two part retraction system of claim 1, wherein the crosslinker is polymethylhydrosiloxane.

4. The two part retraction system of claim 1, wherein the water soluble astringent aluminum salt is potassium aluminum sulfate (AlKSO4), aluminum ammonium sulfate, aluminum sulfate, aluminum chlorohydrate, aluminum acetate, or a mixture thereof.

5. The two part retraction system of claim 1, wherein the hydrophilic additive is potassium polyacrylate, sodium polyacrylate, or siloxylated polyethers.

6. A method of retracting a sulcus of a patient, the method comprising applying a two-part retraction system that expands upon curing using a dispensing device having about a 1 mm outside diameter that can be inserted into the sulcus to form a semi-rigid foam cord, and slowly withdrawing the dispensing device while emptying the two part retraction composition,
   the two-part retraction composition comprising a base paste and a catalyst paste, wherein
   the base paste comprises (1) a crosslinker capable of releasing hydrogen gas upon combination with the catalyst paste having a hydrosilation catalyst at room temperature, (2) a vinyl fluid, (3) a non-reinforcing filler, (4) a reinforcing filler, (5) optionally a hydroxy terminated polydimethylsiloxane, and (6) optionally a hydrophilic additive, and
   the catalyst paste comprises (1) a vinyl fluid, (2) a hemostatic agent, (3) a non-reinforcing filler, (4) a reinforcing filler, (5) a platinum complex hydrosilation catalyst, and (6) a retarder;

the dispensing device comprising first and a second longitudinally juxtaposed barrels; each said barrel having a first and a second end; each said first and second barrels having a quantity of at least one of the materials initially contained therein; each said barrel having an open end and a dispensing end; a sealing plunger disposed in each said barrel such that the material in each said barrel is initially positioned between said dispensing end of said barrels and the respective ones of said sealing plungers; a snap cap contiguously formed to initially close each of said dispensing ends of said barrels; such that said snap cap may be broken from said barrels to form a secondary open end at said dispensing end of said barrels, thereby facilitating the material contained in each said barrel to flow through and be dispensed; wherein the dispensing ends and the snap cap form a neck area as a section of reduced thickness which is defined by a V-groove that runs around the perimeter of the neck area in a figure 8 shape, whereby the V-groove acts to concentrate the stress across the neck in such a way that said snap cap may be broken from said barrels along a breaking plane; wherein said snap cap includes a tab portion opposite the neck area, the tab portion being of a sufficient size to allow a user to apply enough leverage to the tab portion to break said snap cap at the section of reduced thickness.

7. A two part retraction system comprising:
a base paste and a catalyst paste, wherein
the base paste comprises (1) a crosslinker capable of releasing hydrogen gas upon combination with the catalyst paste having a hydrosilation catalyst at room temperature, (2) a vinyl fluid, (3) a non-reinforcing filler, (4) a reinforcing filler, (5) optionally a hydroxy terminated polydimethylsiloxane, and (6) optionally a hydrophilic additive, and the catalyst paste comprises (1) a vinyl fluid, (2) a non-reinforcing filler, (3) a reinforcing filler, (4) a platinum complex hydrosilation catalyst, and (5) a retarder, and
wherein at least one of the base paste or the catalyst paste further includes an encapsulated hemostatic agent.

8. The two part retraction system of claim 7, wherein the crosslinker has a hydrogen content of at least 7 mmol/g.

9. The two part retraction system of claim 7, wherein the crosslinker is polymethylhydrosiloxane.

10. The two part retraction system of claim 7, wherein the hemostatic agent is a water soluble astringent aluminum salt.

11. The two part retraction system of claim 10, wherein the water soluble astringent aluminum salt is potassium aluminum sulfate (AlKSO4), aluminum ammonium sulfate, aluminum sulfate, aluminum chlorohydrate, aluminum acetate, or a mixture thereof.

12. The two part retraction system of claim 7, wherein the hemostatic agent is ferric sulfate, ferric chloride, a mixture of ferric sulfate and ferric chloride, permanganates or zinc chloride.

13. The two part retraction system of claim 7, wherein the hemostatic agent is a mixture of tannins, adrenaline or 8-hydroxyquinoline derivatives.

14. The two part retraction system of claim 7, wherein the hydrophilic additive is potassium polyacrylate, sodium polyacrylate, or siloxylated polyethers.

* * * * *